United States Patent [19]

Slimak

[11] Patent Number: 4,793,991

[45] Date of Patent: Dec. 27, 1988

[54] HYPOALLERGENIC COSMETICS, LIP BALMS AND LIP STICKS

[76] Inventor: Karen M. Slimak, 9207 Shotgun Ct., Springfield, Va. 22153

[21] Appl. No.: 825,657

[22] Filed: Jan. 31, 1986

[51] Int. Cl.$^4$ ...................... A61K 7/027; A61K 35/64
[52] U.S. Cl. .......................................... 424/64; 424/95; 260/420
[58] Field of Search ...................... 424/64, 95; 260/420

[56] References Cited

U.S. PATENT DOCUMENTS 3,211,619 10/1965 Buchwalter et al. ................. 424/64

OTHER PUBLICATIONS

Cosmetic, Toiletry and Fragrance Assoc., cited in Chem. Abstracts, vol. 101: 177251n, 1984.
Morse, "Bees and Beekeeping", p. 181, 1975.
Harry's Cosmeticology, pp. 330, 331, 324, 325, 7th Ed., 1982.
Gay, cited in Chem. Abstracts, vol. 39: 4972, 1945.

Primary Examiner—Johnnie R. Brown
Assistant Examiner—Jacqueline M. Stone
Attorney, Agent, or Firm—Stevens, Davis, Miller & Mosher

[57] ABSTRACT

Hypoallergenic lip balms, lip sticks, and other cosmetic preparations can be prepared from single plant source beeswaxes and vegetable oils.

18 Claims, No Drawings

HYPOALLERGENIC COSMETICS, LIP BALMS AND LIP STICKS

BACKGROUND OF THE PREFERRED EMBODIMENTS (1) Field of the Invention

The present invention is concerned with the utilization of beeswax from single plant sources an ingredient in hypoallergenic lip balms, and lip sticks and other cosmetic preparations.

(2) Description of the Background

Beeswax has been used as an ingredient in cosmetic preparations virtually since the beginning of the cosmetic art. It has been used in countless preparations; however beeswax has always been utilized as one item of commerce when in fact it is many. In the same way that the composition of honey varies depending on the plant source from which the nectar is derived, the composition of beeswax varies according to the plants the bees were feeding on at the time the comb was drawn.

The immediately obvious differences are in color and consistency of the wax, which are occasionally observed. For example, virgin Brazilian pepper beeswax is yellow, and tupelo beeswax is white. These differences have never been considered important nor noticed because the wax is melted downs, combined, processed and formed into blocks.

The differences in plant source are probably only important in the manufacture of hypoallergenic lip balms, lip sticks, and other cosmetic preparations. Allergic people will respond differently to beeswaxes, depending on the plant sources in the mix of beeswaxes, because of responses to plant residues in the wax.

This can be used to an advantage when developing hypoallergenic cosmetic preparations. By selecting beeswaxes from hypoallergenic plant sources and combining them where possible with an oil from the same plant or closely related plant, it is possible to develop almost universally well tolerated cosmetic preparations.

SUMMARY OF THE PREFERRED EMBODIMENTS

It is one object of the present invention to provide beeswaxes from separate, single plant sources for use in hypoallergenic cosmetic preparations.

Another object of the present invention is to provide cosmetic compositions of beeswax and oil, as lip stick ingredients.

It is another object of the present invention to provide cosmetic compositions of beeswax and oil, for use as lip balm.

DESCRIPTION OF PREFERRED EMBODIMENTS

It has now been found that beeswaxes from single plant sources (at least 70% single plant source, preferably 100%) can be used in the production of hypoallergenic lip balms and lip stick preparations.

In one embodiment, a single plant source beeswax is combined with an oil from the same plant source in proportions ranging from 1:1/10 to 1:10, preferably 1:1 by volume to produce a hypoallergenic lip balm in which a single plant source beeswax and single plant source oil are the only ingredients.

In another embodiment, a beeswax from a single plant source is combined with an oil from a closely related plant to form a hypoallergenic lip balm in whch the wax and oil are the primary ingredients.

In another embodiment waxes and oils are not related but generally well tolerated plant sources to produce a hypoallergenic product.

In another embodiment, the above products may be used as a basic ingredient in lip stick preparations.

In another embodiment, the above products are used as basic ingredients in other cosmetic preparations.

EXAMPLE NUMBER 1

AVOCADO LIP BALM

Equal portions by volume melted avocado beeswax and avocado oil are combined and mixed while mixture cools and gradually thickens, to form a hypoallergenic lip balm, and a base for lip stick and other cosmetic compositions.

EXAMPLE NUMBER 2

COMPOSITE LIP BALM

Clover beeswax and soy oil, both from plants in the legume family, are combined in the method of Example 1 to form a hypoallergenic lip balm, a base for lip sticks, and other cosmetic compositions.

EXAMPLE NUMBER 3

LIP BALM

Eucalyptus beeswax and sunflower oil, both hypoallergenic items, are combined in the method of Example 1 to form a hypoallergenic lip balm, lip stick base and cosmetic composition of matter.

As noted in example 2 above, the closely related plant oil is selected from a plant from the same taxonomic family as the plant source used to make the single plant source beeswax. As noted from example 3, eucalyptus is selected as the single plant source for the single plant source beeswax. However, the taxonomic family including eucalyptus contains no plant which will yield an oil. Therefore, a well tolerated plant source oil such as sunflower oil is combined with the eucalyptus beeswax.

Although combination of the single plant source waxes and oils is preferred, this is in no way excludes the use of single plant source waxes in any cosmetic preparations, this use is within the scope of the present invention.

Having now fully described the invention, it will be apparent to one of ordinary skill in the art that many changes and modifications can be made thereto without departing from the spirit of the invention as set forth herein.

What is claimed is:

1. A composition of matter including single plant source beeswax and oil in a cosmetic preparation.

2. The composition of matter of claim 1, wherein the oil is from the same plant source as the plant source of the single plant source beeswax.

3. The composition of matter of claim 1, wherein the oil is from a plant source closely related to the plant source of the single plant source beeswax.

4. The composition of matter of claim 1, wherein the oil is selected from well tolerated oils.

5. The composition of matter of claim 2, wherein the single plant source of both oil and beeswax is avocado.

6. The composition of matter of claim 3, wherein the single plant source of the beeswax is clover, and the plant source of the oil is soy.

7. The composition of matter of claim 4, wherein the single plant source of the beeswax is eucalyptus, and the plant source of the oil is sunflower.

8. The composition of matter of claim 4, wherein the single plant source of the beeswax is Brazilian pepper.

9. The composition of matter of claim 4, wherein the single plant source of the beeswax is tupelo.

10. The composition of matter of claim 1 wherein the cosmetic preparation is a lipstick.

11. The composition of matter of claim 1 wherein the cosmetic preparation is a lip balm.

12. A cosmetic preparation base comprising a single plant source beeswax.

13. The composition of matter of claim 12 wherein the cosmetic preparation is a lip balm.

14. The composition of matter of claim 12 wherein the cosmetic preparation is a lipstick.

15. A method of treating human lips comprising applying a composition including a single plant source beeswax to the lips.

16. A beeswax product, in which a minimum of 70% of the beeswax is from one plant source.

17. The composition of matter of claim 4 wherein the oil is present in the ratio of 1:1/10 to 1:10 as compared to the volume of the beeswax.

18. The composition of matter of claim 17 wherein the oil is present in the ratio of 1:1 as compared to the volume of the beeswax.

* * * * *